United States Patent [19]
Bodicky et al.

[11] 4,304,231
[45] Dec. 8, 1981

[54] CATHETER WITH WIRE STYLET

[75] Inventors: Raymond O. Bodicky, St. Louis; Ronald Crouther, Manchester, both of Mo.

[73] Assignee: Sherwood Medical Industries, Inc., St. Louis, Mo.

[21] Appl. No.: 111,006

[22] Filed: Jan. 9, 1980

[51] Int. Cl.³ .............................................. A61M 5/00
[52] U.S. Cl. ................... 128/214.4; 128/221; 128/349 R
[58] Field of Search ............... 128/214, 214.4, 214.8, 128/221, 348, 349, 350, DIG. 16

[56] References Cited

U.S. PATENT DOCUMENTS

| | | | |
|---|---|---|---|
| 3,515,137 | 6/1970 | Santomieri | 128/214.4 |
| 3,633,579 | 1/1972 | Alley et al. | 128/214.4 |
| 3,672,367 | 6/1972 | Scislowicz | 128/214.4 |
| 3,703,174 | 11/1972 | Smith | 128/214.4 |
| 3,709,223 | 1/1973 | Macalad et al. | 128/214.4 |
| 3,825,001 | 7/1974 | Bennet et al. | 128/214.4 |
| 3,835,854 | 9/1974 | Jewett | 128/214.4 |
| 4,037,600 | 7/1977 | Poncy et al. | 128/214.4 |

*Primary Examiner*—Stephen C. Pellegrino
*Attorney, Agent, or Firm*—Wegner, Stellman, McCord, Wood & Dalton

[57] ABSTRACT

A catheter introducer device using a silicone rubber catheter with a stylet therein permitting introduction by manual threading of catheters which would otherwise be too flexible for individual insertion. The stylet is held at its proximal end by a hub which, with a seating ferrule, abuts a proximal end of the catheter. The hub may be pushed to wedge the catheter in an introducer cannula and is then withdrawn carrying the stylet with it, leaving the catheter in place and ready for use.

10 Claims, 5 Drawing Figures

CATHETER WITH WIRE STYLET

DESCRIPTION

1. Technical Field

This invention relates to a catheter and, more particularly, to a catheter introducer device for inserting a silicone rubber catheter by hand.

2. Background Art

This invention relates to a catheter introducer for inserting a catheter into a passageway, such as a blood vessel. The catheter so inserted is commonly used to inject an intravenous solution or to keep blood vessels free from blockage.

Typical prior devices have required manual manipulation using sheaths and/or gloves to thread the catheter into place. One such device is shown in the Poncy et al U.S. Pat. No. 4,037,600, wherein a catheter is threaded through a V-shaped component after a special needle has been used to form a venipuncture. The catheter is retained in a flexible sleeve and is hand manipulated through the sleeve to thread the catheter into the passageway. The catheter must have sufficient stiffness or integrity to be self-sustaining as it is threaded into the passageway and around bends and joints in the passageway, but cannot be so stiff as to cause damage to the passageway in the event it contacts or hangs up therein as it is being inserted.

Other such threading devices are shown in the Bennet et al U.S. Pat. No. 3,825,001 and the Jewett U.S. Pat. No. 3,835,854 wherein a plastic sheath ('001) or a chamber ('854) are used to store the catheter prior to and during manipulation of the catheter into place.

An improved apparatus was provided by the teachings of the Smith U.S. Pat. Nos. 3,703,174 and 3,826,256 wherein a very flexible catheter (wet noodle limpness) is inserted into a passageway by the use of an introducer cannula and a fluid placed under pressure behind and between the juncture of the catheter and the introducer cannula, which fluid propels the catheter into the passageway for a relatively great distance and at a relatively uniform rate. These flexible catheters have typically been made of silicone rubber. However, because of their high degree of flexibility, they cannot be threaded by hand into a passageway.

Many of todays medical professionals were trained to manually thread catheters into a passageway as taught in the above U.S. Pat. No. 4,037,600 and others. It has been found that these personnel have been reluctant to use the fluid injection systems, such as disclosed in U.S. Pat. Nos. 3,703,174 and 3,826,256. Further, it has been found that these fluid injection systems cannot be used with certain patients, their anatomy being such that the catheter may not be freely injected. Nevertheless, due to production costs, it is desirable to be able to make catheters for both types of injection systems of the same material.

The present invention is directed to overcoming one or more of the problems as set forth above.

DISCLOSURE OF INVENTION

This invention relates to a catheter introducer device wherein a silicone rubber catheter may be manually threaded into a body passageway through an introducer cannula having an enlarged proximal portion. Since a silicone rubber catheter is itself too flexible for such threading, a wire stylet is disposed within the lumen of the catheter as a stiffening member. The catheter has an enlarged proximal portion which seats in the enlarged proximal portion of the introducer cannula to prevent the catheter from being completely threaded into the passageway. A hub carried by the proximal end of the stylet has a seating ferrule which rests against the enlarged proximal portion of the catheter so that when the hub is pushed into the introducer cannula, the enlarged proximal portion of the catheter is seated in the enlarged proximal portion of the introducer cannula. The hub and seating ferrule along with the stylet are then withdrawn from the catheter so that the catheter and introducer cannula can be connected to an I.V. set, or the like.

This device permits the newer silicone rubber catheter to be used with a manual threading technique. Thus, silicone rubber catheters may be used by medical professionals who have been unwilling to use fluid injecting systems and may be used on patients whose anatomy does not permit use of the fluid injecting systems. This device also permits easy and positive seating of the catheter in the introducer cannula and easy withdrawal of the stylet from the catheter. This not only reduces production costs by permitting large numbers of catheters to be silicone rubber, but also it decreases patient discomfort by using a catheter which will be very flexible when in place and during use.

BRIEF DESCRIPTION OF DRAWINGS

FIG. 5 shows the catheter and introducer cannula ready for connection to an I.V. set, or the like.

BEST MODE FOR CARRYING OUT THE INVENTION

Figure 1:
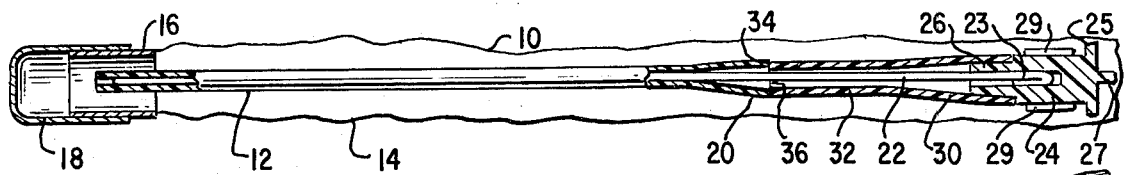
FIG. 1 is a partial cross-sectional view of the catheter introduction assembly of this invention.

In a catheter introduction assembly 10 shown in FIG. 1, a catheter 12 is supplied in a flexible sleeve 14 sealed at a proximal end and having a tubular introducer 16 at its distal end. The assembly 10 contains a cap 18 which closes the opening in the introducer 16 to maintain the assembly in a sterile condition during storage.

The catheter 12 is silicone rubber, or the like, molded to have an enlarged proximal end portion 20. This type of catheter 12 is extremely pliable having a consistency similar to a wet noodle and is presently used with fluid injection systems of the type disclosed in Smith U.S. Pat. Nos. 3,703,714 and 3,826,256. However, these catheters 12 are too pliable to be used with hand threaded systems. Therefore, a spring-wound stylet 22 is extended through the lumen of the catheter 12 and has a crimp 23 at its proximal end for holding the stylet 22 in a stylet hub 24. The stylet 22 adds sufficient stiffness to the catheter 12 to enable the catheter to be threaded into a body passageway by hand. The stylet hub 24 has a radially extending flange 25 on the proximal end thereof with an axially extending web 27 on said flange 25 and radially extending lugs 29 on a cylindrical portion thereof. Said flange 25, web 27 and lugs 29 on the hub 24 are used to turn the stylet 22 in the catheter 12, to turn the catheter 12 and the stylet 22 together, to push the stylet 22 and catheter 12 forward, and to remove the stylet 22 from the catheter 12. The hub 24 has a male luer adaptor 26 on the distal end thereof, which adaptor 26 is wedged into an enlarged portion 30 of a cylindrical seating ferrule 32 which encircles a proximal portion of the stylet 22 adjacent said adaptor 26. The distal end 34 of the seating ferrule 32 has a diameter and a size to match the diameter and size of the proximal end 36 of the enlarged proximal end portion 20 of the catheter 12.

Figure 2:
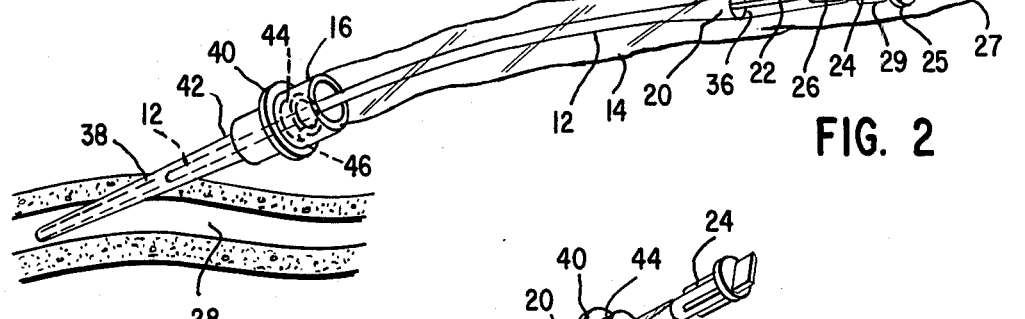
FIG. 2 is a perspective view of the assembly during insertion of the catheter.
Figure 3:
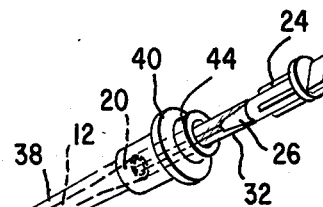
FIG. 3 shows the assembly with the catheter being seated in the introducer cannula.
Figure 4:
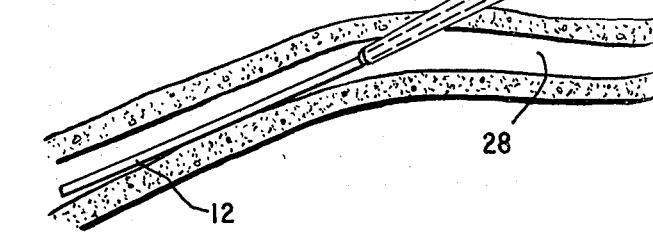
FIG. 4 shows the catheter in place with the stylet and seating ferrule being removed.

FIGS. 2 through 4 show the use of this assembly 10 in introducing the catheter 12 into a body passageway 28. FIG. 2 shows a conventional introducer cannula 38 placed in a body passageway 28 through a venipuncture formed by an introducer needle (not shown) and the introducer cannula 38. A typical method for inserting an introducer cannula is disclosed in Alley et al U.S. Pat. No. 3,633,579. An introducer needle (not shown) is nested in the introducer cannula 38 so that the two form a unit. Preferably, the needle is hollow and has a flashback vent plug, or the like, with the needle point protruding slightly beyond the tip of the introducer cannula 38. Proper insertion into the passageway 28 is indicated by blood flashback into the vent plug. When this occurs, the needle may be withdrawn and the introducer cannula 38 is ready for use to place the catheter 12. A connector hub 40 is affixed to an enlarged tapered proximal portion 42 of the introducer cannula 38. Said connector hub 40 has an outwardly facing collar 44 and an inwardly formed female luer adaptor 46.

With the introducer cannula 38 in place, the cap 18 is removed from the tubular introducer 16 and the catheter 12 is carefully inserted into the end of the introducer cannula 38 whereupon the tubular introducer 16 is coupled around the collar 44 of the introducer cannula 38, as shown in FIG. 2. The catheter 12 may then be grasped through the sleeve 14 approximately one inch behind the introducer 16 and pushed into the cannula 38 and into the body passageway 28 by collapsing the sleeve 14 behind the introducer 16. The sleeve 14 is then stripped back relative to the catheter 12, whereupon another segment of the catheter 12 is grasped and introduced until the enlarged proximal portion 20 starts to enter the connector hub 40. The stylet 22 is positioned in the catheter 12 during the whole introduction so that the threading of the catheter 12 is aided by said stylet 22. This method of introducing the catheter 12 up to this point is the same as taught in the Alley et al U.S. Pat. No. 3,633,579, discussed above, with the exception of the presence of the stylet 22 in the catheter 12.

As shown in FIG. 3, with the enlarged portion 20 of the catheter 12 in the enlarged portion 42 of the cannula 38, the sleeve 14 and introducer 16 may be removed and discarded. By then holding the introducer cannula 38 and pushing the hub 24 and the seating ferrule 32 toward the introducer cannula 38, the distal end 34 of the seating ferrule 32 engages proximal end 36 of the enlarged portion 20 of the catheter 12 to securely wedge the catheter 12 in the proximal portion 42 of the cannula 38.

Figure 5:
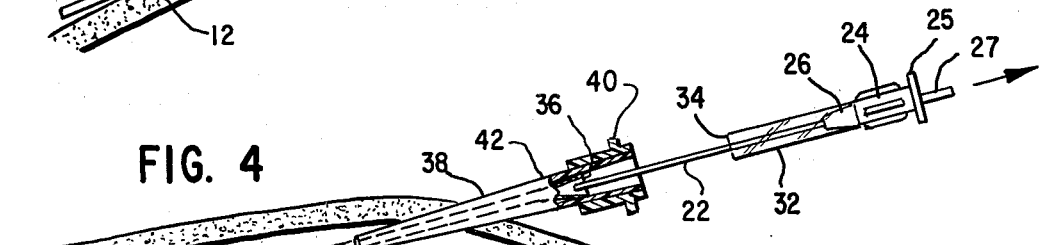
Figure 5:
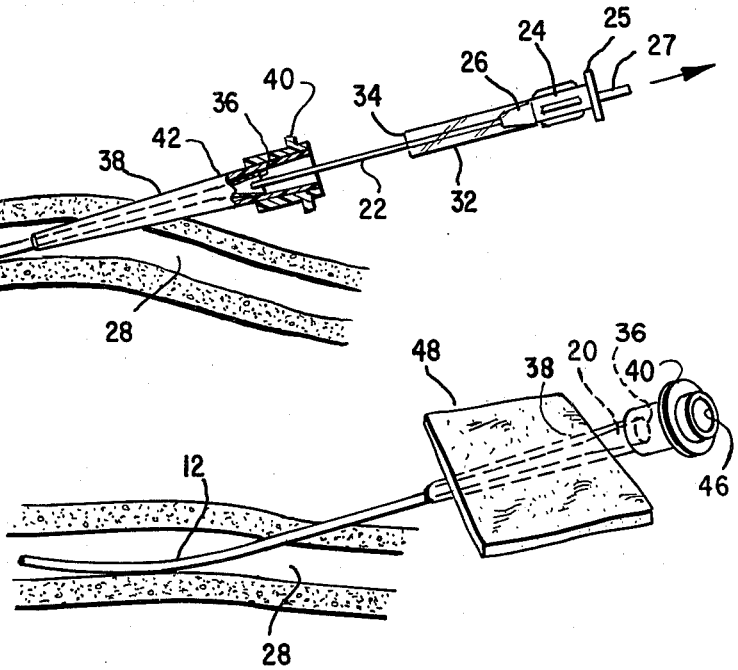

The stylet hub 24 and seating ferrule 32 may then be withdrawn from the introducer cannula 38, pulling the stylet 22 from the lumen of the catheter 12 as shown in FIG. 4. Since the enlarged portion 20 of the catheter 12 is seated in the enlarged portion 42 of the cannula 38, the catheter 12 is not withdrawn with the hub 24 and stylet 22. The stylet 22 will draw blood through the catheter 12 causing flashback when the stylet 22 is entirely removed, indicating proper placement of the catheter 12. The introducer cannula 38 and catheter 12 may then be removed from the venipuncture, as shown in FIG. 5, to leave a desired length of the catheter 12 within the body passageway 28. The introducer cannula 38 is then taped at 48 to the skin so as to reduce irritation to the area around the venipuncture and to assure that the distal end of the cannula 38 will not collapse or cut the catheter 12. An I.V. line may then be connected to the connector hub 40 of the introducer cannula 38.

The device permits introduction of the newer silicone rubber catheters by a conventional method which heretofore could only be used with catheters made of a stiffer material. Further, the stylet hub 24 and seating ferrule 32 ensure both the secure seating of the catheter 12 in the introducer cannula 38 and the easy removal of the stylet 22 from the cannula 12.

Other aspects, objects and advantages of this invention can be obtained from a study of the drawings, the disclosure and the appended claims.

We claim:

1. In a manual catheter introducer having an introducer cannula having a hub with an enlarged proximal portion, the improvement comprising:
   an elongated catheter made of a soft, pliable material having a lumen throughout the length thereof;
   an enlarged proximal portion on said catheter;
   a stylet disposed within the lumen of said catheter and extending substantially the full length thereof; and
   seating means carried by said stylet and axially abutting said enlarged proximal portion of said catheter for seating said catheter in said introducer cannula with the enlarged proximal portion of the catheter wedged into the enlarged proximal portion of said introducer cannula.

2. The improvement of claim 1, wherein said enlarged proximal portion of said catheter is integrally formed therewith.

3. The improvement of claim 1, wherein said stylet is spring-wound wire.

4. The improvement of claim 1, wherein said seating means comprises:
   a ferrule carried by said hub and abutting said catheter.

5. The improvement of claim 1, wherein a sleeve is disposed around the catheter and stylet through which the catheter may be grasped for manual threading of the catheter and stylet into a body passageway.

6. The improvement of claim 5, further comprising a tubular introducer on the distal end of said sleeve wherein the proximal end of the introducer cannula may be nested within said tubular introducer during insertion of the catheter and stylet.

7. In a catheter introducer having an introducer cannula with an enlarged proximal portion and a catheter with a stylet nested throughout the length thereof, the improvement comprising:
   an enlarged proximal end portion on said catheter;
   a hub carried by the proximal end of the stylet; and
   a ferrule carried by the hub and surrounding said stylet, said ferrule abutting said enlarged proximal end portion of said catheter;
   wherein said enlarged proximal end portion of the catheter is seated in the enlarged proximal portion of the introducer cannula by pushing said hub and ferrule against said catheter.

8. The improvement of claim 7, wherein the catheter remains seated when said hub and stylet is withdrawn so as to remove the stylet from the catheter.

9. The improvement of claim 7, further comprising a sleeve around the catheter and stylet through which the catheter may be grasped for manual threading of the catheter into a body passageway.

10. The improvement of claim 9, further comprising a tubular introducer on the distal end of said sleeve wherein the proximal end of the introducer cannula may be nested within said tubular introducer during insertion of the catheter and stylet in said introducer cannula.

* * * * *